(12) United States Patent
Lerner

(10) Patent No.: US 6,913,763 B2
(45) Date of Patent: Jul. 5, 2005

(54) METHOD AND DEVICE FOR ENHANCED DELIVERY OF A BIOLOGICALLY ACTIVE AGENT THROUGH THE SPINAL SPACES INTO THE CENTRAL NERVOUS SYSTEM OF A MAMMAL

(75) Inventor: Eduard N. Lerner, Amsterdam (NL)

(73) Assignee: Intrabrain International NV, Curacao (AN)

( * ) Notice: Subject to any disclaimer, the term of this patent is extended or adjusted under 35 U.S.C. 154(b) by 318 days.

(21) Appl. No.: 10/050,183

(22) Filed: Jan. 18, 2002

(65) Prior Publication Data

US 2002/0082583 A1 Jun. 27, 2002

Related U.S. Application Data

(63) Continuation-in-part of application No. 09/197,133, filed on Nov. 20, 1998, now Pat. No. 6,410,046, which is a continuation-in-part of application No. 09/077,123, filed on May 20, 1998, now Pat. No. 6,678,553, and a continuation-in-part of application No. PCT/EP96/05086, filed on Nov. 19, 1996.

(51) Int. Cl.[7] .................................................. A61F 2/02
(52) U.S. Cl. ...................................................... 424/423
(58) Field of Search ................................... 424/423, 434

(56) References Cited

U.S. PATENT DOCUMENTS

| 4,349,023 | A | 9/1982 | Gross |
|---|---|---|---|
| 4,518,383 | A | 5/1985 | Evans |
| 4,564,016 | A | 1/1986 | Maurice et al. |
| 4,883,660 | A | 11/1989 | Blackman et al. |
| 5,087,243 | A | 2/1992 | Avitall |
| 5,169,384 | A | 12/1992 | Bosniak et al. |
| 5,222,936 | A | 6/1993 | Stephen et al. |
| 5,232,441 | A | 8/1993 | Stephen et al. |
| 5,401,239 | A | 3/1995 | Stephen et al. |
| 5,486,160 | A | 1/1996 | Rossi et al. |
| 5,545,617 | A | 8/1996 | Dartt et al. |
| 5,588,961 | A | 12/1996 | Leone et al. |
| 5,728,068 | A | 3/1998 | Leone et al. |
| 5,807,306 | A | 9/1998 | Shapland et al. |
| 5,843,016 | A | 12/1998 | Lugnani et al. |
| 5,897,858 | A | 4/1999 | Haslwanter et al. |
| 6,219,557 | B1 | 4/2001 | Havinis |
| 6,410,046 | B1 * | 6/2002 | Lerner ........................ 424/434 |

OTHER PUBLICATIONS

E. Lerner et al, Clinical Autonomic Research vol. 10 (4) pp. 246–247 (2000).

* cited by examiner

Primary Examiner—Carlos A. Azpuru
(74) Attorney, Agent, or Firm—Nixon & Vanderhye P.C.

(57) ABSTRACT

A delivery method and implantable apparatus that allows for controlled, enhanced and (pre)-programmable administration of a biologically active agent into the spinal structures and/or the brain via the epidural space of a mammal, particularly of a human being and including a feedback regulated delivery method and apparatus specifically in the treatment of neurological diseases and chronic pain.

23 Claims, 4 Drawing Sheets

METHOD AND DEVICE FOR ENHANCED DELIVERY OF A BIOLOGICALLY ACTIVE AGENT THROUGH THE SPINAL SPACES INTO THE CENTRAL NERVOUS SYSTEM OF A MAMMAL

CROSS REFERENCE TO RELATED APPLICATIONS

This application is a continuation-in-part of U.S. Ser. No. 09/197,133 filed Nov, 20, 1998, now U.S. Pat. No. 6,410,046: a continuation-in-part of U.S. Ser. No. 09/077,123 filed May 20, 1998, now U.S. Pat. No. 6,678,553 and continuation-in-part of PCT/EP96/05086 of Nov, 19, 1996.

FIELD OF THE INVENTION

The present invention relates to a delivery method and implantable apparatus that allows for controlled, enhanced and (pre)-programmable administration of a biologically active agent into the spinal structures and/or the brain via the epidural space of a mammal, particularly of a human being.

BACKGROUND OF THE INVENTION

Currently, there are a large number of methods and devices available to deliver intraspinal medications and the majority of them are based on continuous infusion by means of spinal catheters. Mostly the drugs for spinal delivery are anaesthetics. Presently two types of spinal anaesthesia techniques are routinely employed in surgical procedures. The two techniques are epidural and subarachnoid or intrathecal anaesthesia. With epidural anaesthesia, a catheter is usually placed in the spinal epidural space and the anaesthetics are administered through the catheter. U.S. Pat. No. 4,349,023 to Gross describes an example of such an epidural procedure. The advantage of this technique is that it allows for continuous administration over an extended period of time. There are however also disadvantages associated to this technique such as for instance, the non-uniform and often unpredictable distribution of the anaesthetics in the epidural space, which can be attributed to the characteristics of the epidural tissue, which is composed of fatty and fibrous material.

In contrast to the epidural space, the subarachnoid or intrathecal space is composed of a far more liquified and thus a faster, more uniform and more predictable distribution medium. Delivery of anaesthetics directly into the spinal subarachnoid space would therefore be preferable, were it not for one major side effect. The major problem is the severe post-operative headaches that often result from the puncture of the dural membrane (or dura) upon entrance of spinal catheters and needles into the subarachnoid space. Furthermore, the use of catheters and particularly small-bore catheters has been implicated in such complications as cauda equina syndrome, a neurological syndrome that is characterised by loss of sensation or mobility of the lower limbs. In May 1992, the FDA alerted Anaesthesia Care Providers to the serious hazard associated with continuous spinal anaesthesia by small bore catheters and has taken action to remove all small bore catheters from the market. An example of the intrathecal administration procedure is described in U.S. Pat. No. 4,518,383 to Evans.

The current method for intrathecal treatment of chronic pain is by means of an intrathecal pump, such as the SynchroMed. RTM Infusion System, a programmable, implanted pump available from Medtronic Inc., of Minneapolis, Minn. The system includes a catheter and a pump section. The pump section comprises a collapsible reservoir and a fill port for refilling the reservoir with fresh drug formulation. The system automatically delivers a controlled drug amount through the catheter by means of an electric peristaltic pump. The dosage, rate and timing can be externally programmed using radio waves. The SynchroMed.RTM Infusion System thus solves long-term delivery and dosage accuracy problems of other existing devices. At present the SynchroMed.RTM is used for spinal delivery of antinociceptive or antispasmodic therapeutics; because of the short half-life of these substances they require frequent readministration, and this is realized by the implanted pump. Although, the system has some major advantages over other existing methods, it also has some disadvantages. One disadvantage is the large, bulky size of the SynchroMed.RTM pump. Due to its size, the device must typically be implanted in the abdominal cavity of a patient and an extended catheter has to be passed through the patient's body to deliver the drug to the desired site of administration. In addition to problems with size and placement, the SynchroMed is burdened by complex electronics for both programming and pumping functionality. Furthermore, complications may arise as a result of the required surgical implantation and the possibility of leakage of the catheter as well as of the pump.

There is thus a need for an alternative spinal delivery method that reduces the risks associated with intrathecal drug delivery such as post-operative headache, meningitis, paralysis and even death by utilising the epidural delivery route. Further there is a need for a novel spinal delivery method that also reduces the surgical risks and disadvantages seen with implantable pump systems such as the SynchroMed.RTM Infusion System. The present invention discloses a method and apparatus that relates to controlled and enhanced epidural delivery of a biologically active agent.

The therapeutic efficacy of numerous highly effective biologically active agents (e.g. large compounds, hydrophilic and charged substances such as for example: proteins, (poly) peptides, and nucleotides) is limited, because they cannot or poorly penetrate the epidural space and other biological barriers, resulting in sub-therapeutic drug levels within the spinal structures and the brain. Distribution from the matrix of a polymeric implant or catheter of a spinal delivery device is based on passive diffusion, which is a slow process. During diffusion the compound (e.g. a peptide) may be subjected to substantial metabolism and clearance. As a result, the volume of tissue exposed to this compound is very small. Thus, due to the lipophilic nature of the epidural space, transport rate and migration distance of hydrophilic and/or ionised compounds within the epidural space is very low. In order to achieve therapeutic adequate levels substantially higher doses will be required in comparison to subarachnoid administration. Whereas subarachnoid administration is a more complicate surgical procedure accompanied with more risks such as post-operative headache, meningitis, paralysis and even death.

Therefore, there is also a large interest in development of a spinal drug delivery method that promotes fast and enhanced transport of therapeutic agents especially of large, hydrophilic and charged substances to the spinal structures and/or the brain (central nervous system, or CNS) for a long term period and that requires a minimum of surgical intervention and offers a minimum of side effects.

The present invention overcomes the disadvantages associated with existing implantable delivery methods such as, bulky reservoirs and/or pumps and the limited drug penetration depth by using phonophoresis or iontophoresis as a drug delivery enhancement technique. Iontophoresis has been defined as the active introduction of ionised molecules into tissues by means of an electric current. Iontophoresis devices require at least two electrodes, both being in electrical contact with some portion of a biological membrane surface of the body. One electrode commonly referred to as the "donor" or "active" electrode, is the electrode from which the biologically active agent, such as a drug or prodrug, is delivered into the body. Another electrode having an opposite polarity functions to complete the electric circuit between the body and the electrical power source. This electrode is commonly referred to as the "receptor" or "passive" electrode. During iontophoresis an electrical potential is applied over the electrodes, in order to create an electrical current to pass through the drug solution and the adjacent tissue.

Iontophoretic drug administration into body cavities by means of a catheter type of electrode has been first disclosed about 95 years ago. The Russians were in this field very productive and during the 1970's and 1980's a considerable number of patents were issued (e.g. SU Nos 532,890; 843,999; 1,005796). Recently, patents have been issued that disclose the treatment of blood-vessel related disorders (e.g. restenosis), bladder, uterus, urethra and prostate disorders.

U.S. Pat. Nos. 6,219,557; 5,588,961; 5,843,016; 5,486,160; 5,222,936; 5,232,441; 5,401,239 and 5,728,068 disclose different types of iontophoresis catheters for insertion into hollow, tubular organs (bladder, urethra and prostate) or into blood vessels.

An implantable system for myocardial iontophoretic delivery of drugs to the heart is disclosed in U.S. Pat. No. 5,087,243.

Reference may be made to U.S. Pat. No. 5,807,306, which describes an iontophoresis catheter device for delivering a drug contained in a polymer matrix into internal tissue. The disclosed catheter may thus be an ideal tool for selective and controlled delivery to any body passageway or hollow organ. Because the drug is contained in a polymeric matrix, the risk of leakage typically associated with catheter devices is practically negligible. However, the disclosed device is not an implantable device and thus not suitable for long-term treatment. Further, the device requires manual operation.

The method of the present invention allows among other treatments also for an improved treatment of chronic pain by means of spinal delivery of anaesthetics or analgesic agents. At present there are no adequate objective measures of pain. The drug is being administered largely based on the sensation of pain expressed by the patient himself. It is however, not possible to measure the extent or amount of pain, whereas this may be of utmost importance for determining the correct drug dosage. It has been suggested that the autonomic nervous system (ANS) may provide information regarding the presence of pain, because the ANS responds in order to maintain homeostasis within the organism to any internal or external stimulus thus also to pain. At present, the assessment of ANS activity is largely focused on the cardiovascular system. Unfortunately, cardiovascular measures such as blood pressure, heart rate and heart rate variability are not reliable indicators for the presence of pain. Skin potentials have been shown to be indicative for the presence of pain. Skin potentials or the sympathetic skin response reflect sweat gland activity and these glands are innervated by sympathetic C-fibers. However, the skin potentials are also largely influenced by the subject's response to emotional stimuli. Thus any emotional stimuli other than pain will influence the measurement. Other disadvantages of skin potentials are the fact that they are unstable and not reproducible.

I have also discovered the presence of fast oscillating potentials within the skin recorded potentials These so-called "fast waves" could not be blocked with atropine meaning that they are not transmitted by M-cholinergic sympathetic nerve fibers such as those innervating the sweat glands. The inventor also discovered that the "fast waves" are not subject to habituation such as "normal" skin potentials do. It has been hypothesised that these "fast waves" reflect sympathetic activity of autonomic brain centres that are most likely not located in the limbic system and are therefore not influenced by the emotional status of the subject. The "fast waves" can be recorded from the skin as well as from any conductive internal body part. It is further suggested that a change in a "fast waves" signal may be used as a tool for pain detection, because they are of autonomic nervous system origin and contain relevant information concerning changes in the internal environment. The detection of such a change in the "fast waves" could thus provide an excellent objective measure for the presence of pain and it may even be detected before the subject has become aware of the pain.

SUMMARY OF THE INVENTION

The present invention relates to a delivery method and device for enhanced and controlled delivery of a biologically active agent into the spinal structures and/or the brain. More particularly, the present invention relates to an implantable device comprising an amount of a biologically active agent and transport means for active transport of the biologically active agent from the device into the epidural space from where it is actively transported through the dura mater into the subarachnoid space and into the CNS.

In view of the limitations of existing spinal delivery systems, it is an object of the present invention to provide a method and device for enhanced and controlled administration of a biologically active agent that allows for effective concentrations of said agent in the spinal structures and/or brain following epidural administration.

It is further an object of the present invention to provide a method and an implantable device for administering a biologically active agent into the spinal structures and/or brain that allows for easy accessibility and convenient localisation to the site of administration in the epidural space of a mammal and particularly a human being.

It is also an object of the invention to provide an implantable device of such design and made of such materials, as well as such a method for administration of a biologically active agent into the spinal structures and/or brain through the epidural space that promotes high patient compliance and acceptance.

It is still another object of the invention to provide a method and an implantable device for administration of a biologically active agent into the spinal structures and/or brain through the epidural space enhanced by iontophoresis and/or phonophoresis that allows for a high level of safety with minimal local and systemic side effects.

It is yet another object of the invention to provide a method and device for controlled and enhanced delivery of a biologically active agent into the spinal structures and/or the brain that is regulated by a feedback signal.

It is further an object of the present invention to provide an excellent method for treatment CNS disorders.

A further object of the present invention is to provide a method and device for controlled and enhanced administration of anaesthetics, analgesic or antinociceptive agents in the treatment of chronic pain whereby the delivered dose is regulated by an integrated feedback system.

These and other objects are accomplished by providing an implantable delivery system based on physical enhancement by means of iontophoresis and/or phonophoresis for delivery of a biologically active agent into the epidural space and from there into the intrathecal space and into the CNS thereby essentially avoiding the systemic blood circulation.

For the purpose of this invention, "iontophoresis" is defined as any form of electrotransport of a substance through mammalian tissue induced or enhanced by the application of an electrical potential. Thus, the term "iontophoresis" as used herein includes without limitation previously defined terms such as iontophoresis, electrotransport, iontokinesis and electroosmosis, and the combination of thereof, which comprises the transport of a substance induced or enhanced by the application of an electric potential.

The term "phonophoresis" as used here is defined without limitation as any form of transport of substances that include non-ionized molecules through mammalian tissue induced or enhanced by the application of ultrasound.

As used in conjunction with the disclosed invention, the term "biologically active agent" as defined herein, is an agent, or its pharmaceutically acceptable salt, or mixture of compounds, which has therapeutic, prophylactic, pharmacological, physiological or diagnostic effects on a mammal and may also include one compound or mixture of compounds that produce more than one of these effects. Suitable therapeutic, pharmacological, physiological and/or prophylactic biologically active agents can be selected from the following listed, and are given as examples and without limitation: amino acids, anabolics, analgesics and antagonists, anaesthetics, anti-adrenergic agents, anti-asthmatics, anti-atherosclerotics, antibacterials, anticholesterolics, anti-coagulants, antidepressants, antidotes, anti-emetics, anti-epileptic drugs, antifibrinolytics, anti-inflammatory agents, antihypertensives, antimetabolites, antimigraine agents, antimycotics, antinauseants, antineoplastics, anti-obesity agents, anti-Parkinson agents, antiprotozoals, antipsychotics, antirheumatics, antiseptics, antivertigo agents, antivirals, appetite stimulants, bacterial vaccines, bioflavonoids, calcium channel blockers, capillary stabilizing agents, coagulants, corticosteroids, detoxifying agents for cytostatic treatment, diagnostic agents (like contrast media, radiopaque agents and radioisotopes), drugs for treatment of chronic alcoholism, electrolytes, enzymes, enzyme inhibitors, ferments, ferment inhibitors, gangliosides and ganglioside derivatives, hemostatics, hormones, hormone antagonists, hypnotics, immunomodulators, immunostimulants, immunosuppressants, minerals, muscle relaxants, neuromodulators, neurotransmitters and nootropics, osmotic diuretics, parasympatholytics, parasympathomimetics, peptides, proteins, psychostimulants, respiratory stimulants, sedatives, serum lipid reducing agents, smooth muscle relaxants, sympatholytics, sympathomimetics, vasodilators, vasoprotectives, vectors for gene therapy, viral vaccines, viruses, vitamins, oligonucleotides and derivatives, and any therapeutic agent capable of affecting the nervous system.

Examples of biologically active agents, which may be preferentially administered using the method disclosed here for enhanced delivery directly into the spinal structures and/or brain and thereby essentially avoiding the systemic circulation include those biologically active agents degraded in the gastrointestinal tract, metabolised in an internal organ or in the blood, rapidly excreted from the bloodstream (e.g. through kidney clearance), and those with limited penetration of the blood-brain barrier. Also, those agents with systemic side effects will benefit from direct administration in the CNS avoiding the blood stream. Further those biologically active agents that at least partly target the CNS although the underlying disease may have systemic clinical manifestations (e.g. alpha-2-agonists and hypertension).

Other objects, features and advantages will be apparent from the following detailed description of preferred embodiments taken in conjunction with the accompanying drawings in which:

DETAILED DESCRIPTION OF PREFERRED EMBODIMENTS

Figure 1:
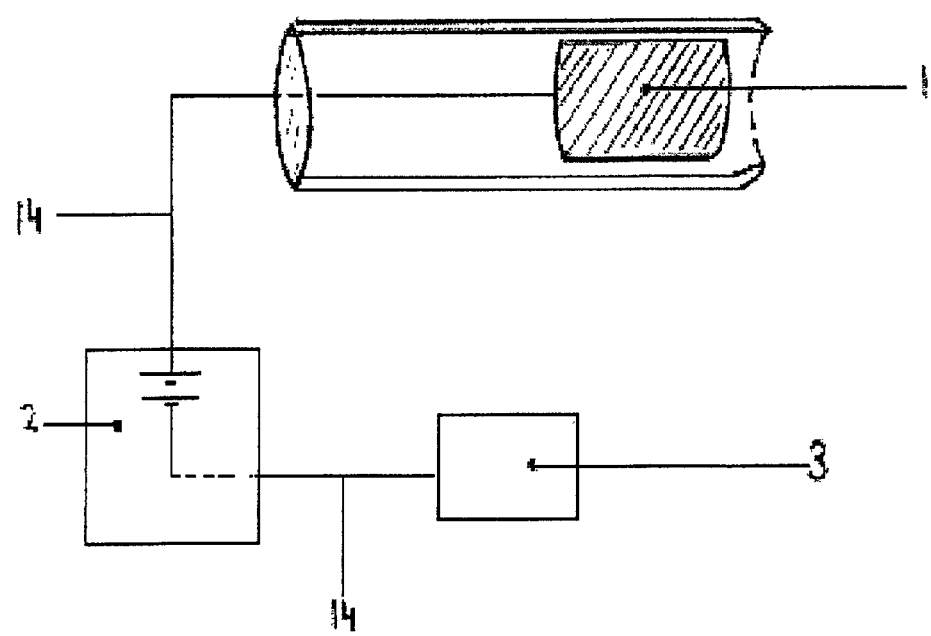
FIG. 1 is schematic representation of the drug delivery device of the present invention.

Practicing the invention involves inserting a donor or active electrode as by a catheter-based device into the epidural space of a mammal and particularly a human being. The catheter may be positioned in the epidural space by any one of numerous well-known methods such as for example the use of a guide wire and fluorescence visualisation. Another electrode being a receptor or passive electrode for iontophoresis may be implanted in the abdomen or any other internal body location but preferably in vicinity of the donor electrode. Power to the electrodes is provided to develop an electric field radiating outward from the donor electrode to the receptor electrode. In order to reduce the risk of cardiac arrhythmia when the electrodes are in the region of the heart, the current to the electrodes may be pulsed on during systole phase of cardiac pumping and off during diastolic phase. The electric field will cause the biologically active agent to permeate outwardly from the donor electrode toward the receptor electrode thus causing transport of the biologically active agent through the epidural space, dura mater, subdural space and eventually through the arachnoid membrane into the intrathecal space from where it may travel to other spinal structures and into the CNS.

The term "catheter" as used in the present invention is intended to broadly include any medical device designed for percutaneous introduction and insertion into a body passageway or a localised area of internal tissue to permit injection or withdrawal of fluids, to keep passage open, to deliver drugs or other therapeutics, or for any other purpose. For purposes of this invention, a catheter is not necessarily tubular. It is contemplated that the drug delivery apparatus of the present invention has applicability for use in the epidural space of a mammal and particularly a human being.

The preferred drug transport means is iontophoresis which facilitates both transport of the drug out of the device and/or tissue penetration, including the epidural space, dura mater, subdural space, arachnoid membrane, subarachnoid space, pia mater and other nervous tissue in the spinal region and further the CNS. Another preferred drug transport means is phonophoresis. In a yet other preferred embodiment the drug transport means is iontophoresis in combination with phonophoresis.

In accordance with the method of the present invention there is provided an implantable catheter-based device for enhanced and controlled delivery of a biologically active agent comprising a donor electrode having an electroconductive member and a drug reservoir or drug transfer part that is in electric contact with the electroconductive member. The drug reservoir or drug transfer part may be expandable or may be part of an expandable member in order to make an intimate contact with the dura mater. This is relevant for those embodiments that are based on iontophoretic delivery of a biologically active agent directly through the dura mater. The device further comprises a receptor electrode having an electroconductive member and an electrolyte-containing compartment. The device according to the present invention further comprises a power control unit (PCU) having integrated a (pre)-programmable power source, which is operated by a microprocessor or microchip and that further includes means for storing and/or transmitting data for example by telemetry. The power control unit is electrically connected to the donor and receptor electrodes.

The PCU can be programmed to deliver any type of current waveform as for example, direct current or alternating current and the current may have any frequency depending on the compound to be delivered and the treatment that requires delivery of said compound. The current strength, duration of current application and location of the receptor electrode may be varied to further focus the flow of the biologically active agent. Thus the direction and uniformity of dispersion and permeation of the biologically active agent may be controlled. The polarity of the donor and receptor electrode is selected with reference to the sense of the ionic compound. The current strength delivered to the donor and receptor electrodes ranges between 0.001 to 10 $mA/cm^2$, and is preferably selected from the following range of 0.01 to 1.0 $mA/cm^2$.

In a preferred embodiment of the present invention the PCU can be externally programmed in order to adjust the delivery dose of the biologically active agent by a physician. Optionally, the delivery device may comprise means for telemetry that allows the physician to receive operational information of the device from a remote site.

In another embodiment the delivery device may comprise a source of thermal energy. Such a source can, of course also be combined with the electric current or ultrasound source. For example, a combination of a source of electric energy and a source of thermal energy has the advantage that a compound with a relatively high molecular weight can be delivered in a mammal, because the supply of thermal energy will allow a better penetration into tissues due to dilatation effects.

The donor electrode of the implantable device as disclosed in the present invention consist of a drug reservoir or drug transfer part, which can release the biologically active agent over an extended period of time while at the same time preserving the bioactivity and bioavailability of the biologically active agent.

After positioning of the catheter-based device in the epidural space, the donor electrode is advanced outward of the device thereby exposing at least partly the drug delivery part of the device into the epidural space. Upon application of an electric field or ultrasound the biologically active agent is actively transported out of the device and travels under influence of the electric field or the applied ultrasound via the epidural space in a direction of the spinal cord to the adjacent spinal tissues and into the brain.

In an expedient embodiment of the disclosed method, the delivery part of the catheter-based device is arranged and constructed in such a way and having such a shape that it is adapted to make an intimate contact with the dura mater. Upon application of an electric field or ultrasound the biologically active agent is then actively transported out of the device and will travel under influence of the electric field or the applied ultrasound through the dura mater into the adjacent spinal tissues.

According to an alternate embodiment of the disclosed method, the delivery device comprises a biosensor that is connected to the PCU. The biosensor may detect any physical or chemical signal upon which the PCU starts, continues and/or modifies or interrupts a delivery program. In this way a feedback mechanism is provided that automatically controls the output current while for example monitoring the physiological condition of the treated subject. An example of the use of such a feedback mechanism is the detection of pain by using signal analysis of the sympathetic "fast waves" during delivery of analgesics in the treatment of chronic pain. The sensor detects these potentials and they are processed and integrated within the PCU by a microprocessor that on its turn uses the processed information as a signal to start, modify or interrupt a particular current delivery program. Normalisation of the signal can be used as indicator for the PCU to stop a particular delivery program.

The biosensor as used in the present invention may be selected from the type of sensors that are sensitive for the following non limiting signals known to those skilled in the art: physical (e.g. temperature, pressure, current strength, potentials as fast waves, skin potentials, EEG, ECG etc.) or chemical (e.g. pH, electrochemical potential, concentration, etc.). Any appropriate sensor may be integrated in or connected to the delivery device according to the present invention and the type of sensor being dependent on the purpose of the delivery application.

In an alternative embodiment, the receptor or passive electrode may comprise a plurality of implanted electrodes (more than one) with preferred site of positioning on the ventral site of the vertebral column as for example the abdomen. The positioning of the receptor electrode is crucial, because it has to create a vector of electrical field in such direction that it facilitates transport of the biologically active agent from the administration site into the spinal structures and/or the brain.

According to yet another embodiment the receptor electrode (s) may be positioned external (e.g. on the skin) of a mammal's body.

The biologically active agent may be delivered by means of a catheter-based device using several different embodiments. In one embodiment, which may be used with any of the catheter embodiments set forth, the biologically active agent is incorporated within a polymer matrix, and this matrix may optionally be applied as a coating on an expandable member of the delivery device. The polymer matrix preferably has good drug holding capacity.

In another embodiment, microspheres incorporating the biologically active agent may be used for delivery of said agent. The drug-laden microspheres may then be injected in the epidural space, near the dura mater and activated by the catheter thereby driving the biologically active agent from the microspheres into the dura mater and the adjacent spinal tissues. Microspheres useful in the present invention include those sold under the name biSphere. TM. available from POINT Biomedical (San Carlos, Calif.).

Additionally, normal drug delivery means may be used as well, such as free liquid form. However, use of polymer matrices has certain advantages over free fluid delivery. Delivery of a biologically active agent, which is contained in a polymer matrix, does not require additional lumens in the catheter to transport the liquid drug solution into and out of the delivery site. Additionally the polymer matrices eliminate the risk of downstream leakage of drug solution, thereby avoiding the risk of exposure of non-target tissue to high concentrations of the biologically active agent. Importantly there will also be no need for implanted pumps that re-administer the drug solution to the implanted catheter and its reservoir Also, since no extra lumens in the catheter are required, the device is narrower and this improves its maneuverability in the body and reduces its production costs.

In an alternate preferred embodiment the device according to the present invention has a mean that allows for in situ refilling of the drug reservoir or drug transfer part. Re-filling methods and devices are well known to those skilled in the art and mechanisms that prevent leakage, back flow of liquid into the filling tube and other problems associated with refillable implants may be used and are well known to those skilled in the art and are enclosed herein their entirety. However, it is expected that the drug reservoir or drug transfer part of the implanted delivery device having an appropriate size could release sufficient quantities of the biologically active agent for at least one year, because the absolute amounts of most biologically active agents required for spinal delivery are very small.

Preferred embodiments of the invention as well as alternative embodiments will be described in detail with reference to the drawings.

In FIG. 1 there is shown a schematic representation of the delivery device. In this FIG. a device is shown that is especially suitable for long-term epidural placement. The three basic components of the delivery device i.e. donor 1 and receptor 3 electrodes and the PCU 2 are contained in insulating and non-degradable, biocompatible housings. The PCU is electrically connected with the two electrodes by insulated electric wires 14.

Figure 2A:
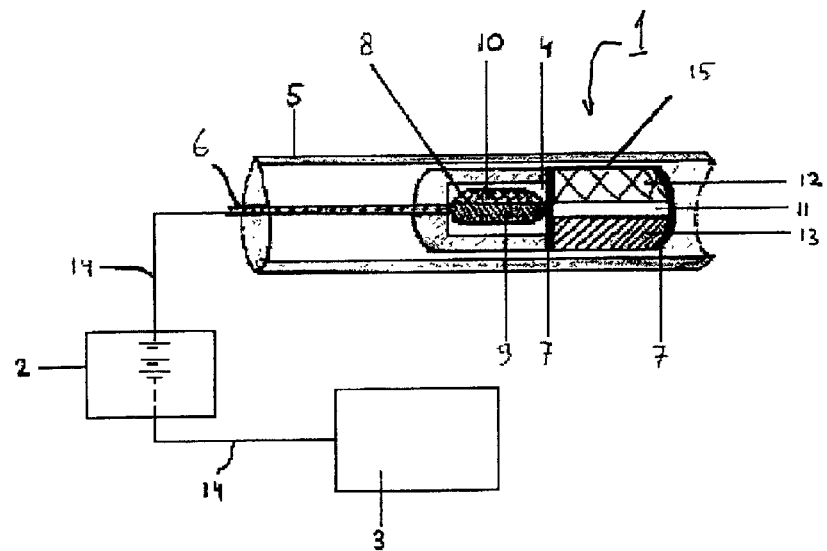
FIG. 2A is a schematic side view, partially in section, of a preferred embodiment of the drug delivery system of the present invention in the form of an expandable drug reservoir or drug transfer part and transport means (iontophoresis electrode) in its inactivated state, positioned in an elongated tubular body.
Figure 2B:
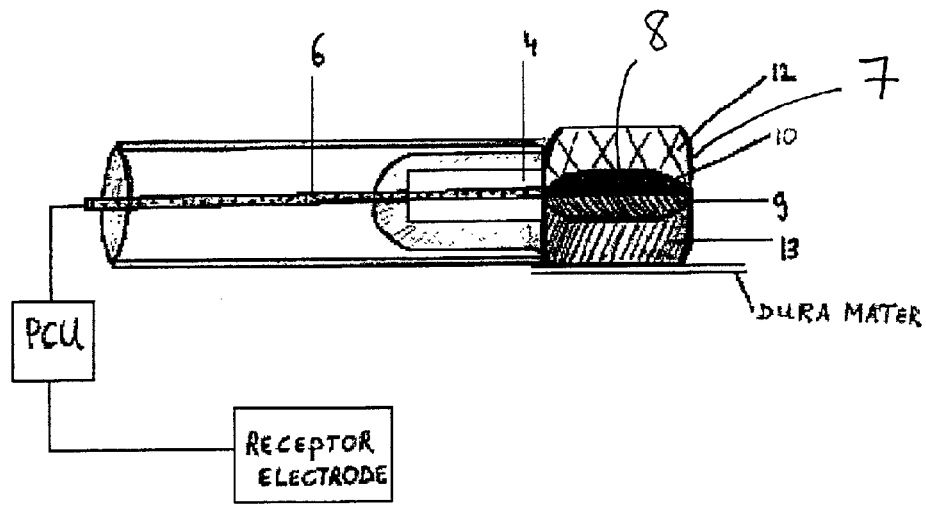
FIG. 2B is a schematic side view, partially in section, of a preferred embodiment of the drug delivery system of the present invention in the form of an expandable drug reservoir or drug transfer part and transport means (iontophoresis electrode) in its "activated", expanded state and, the drug reservoir and/or drug transfer part being positioned outside the elongated tubular body and in contact with the dura mater.

In order to provide an intimate contact with the dura mater the drug delivery part or drug transfer part may be expanded. The means of expansion of the drug delivery part of the device according to the present invention include without limitation the following:

1. The drug transfer part becomes expanded due to pushing into its central space or potential space the central piece 8, which could also serve as an electrode that could be shaped as a rod or have another shape or design such as a spring loaded or manually loaded wire basket of various shapes obvious to those skilled in the art, into the interior chamber 11 of the drug transfer part 13 (FIG. 2A; non-expanded, and FIG. 2B; expanded). The drug reservoir or drug transfer part of the drug delivery device is advanced out of the catheter shaft 5, whereafter the middle piece 8 is pushed into the drug transfer part by a wire or rod 6, that may be attached to a handle of the device outside the epidural space. The part of the expandable device not involved in drug transfer is composed of an insulating, impermeable and biocompatible material (e.g. polymer) 12. The means of expansion is preferable supplied with appropriate markings to indicate the amount of expansion of the expandable part of the device. The middle piece 8 comprises a part that is not electroconductive 10 and an electroconductive part 9 that serves as an electrode for iontophoresis and is via 6 and 14 connected to the PCU 2. The PCU may be placed at any convenient internal position; the electric circuit is completed by connection of the receptor electrode(s) 3 on a pre-determined location internal to the body (e.g. within the abdominal region just under the skin but outside the peritoneal membrane) or optionally on a determined external location of a human or other mammal's body, e.g., just outside the skin over the abdominal region.

The wire or rod 6 may be used to conduct current to the electrode 9 after the electrode is in place. When the device has to be removed, the middle piece 8 is removed from the expandable member of the delivery device and is preferably pulled into holding chamber 4 using wire 6. This allows the delivery device to assume its narrower profile, which aids in the removal of the device from the epidural space. Optional impermeable end caps 7 are provided at both anterior and posterior ends of the drug transfer part to prevent inadvertent drug leakage as well as to prevent delivery of the biologically active agent into non-target tissue. The posterior end caps are constructed in such a way to prevent the central piece to be pushed too far through the electrode space 11, outside markers indicate the position of the middle piece 8.

2. Alternatively to mechanical induced expansion, the polymeric matrix of the drug reservoir has reversible swelling properties induced by electric current, pH, temperature or any combinations thereof or by any other possible chemical or physical parameter, which may induce reversible swelling of the polymeric drug reservoir, known to those skilled in the art.

Figure 3A:
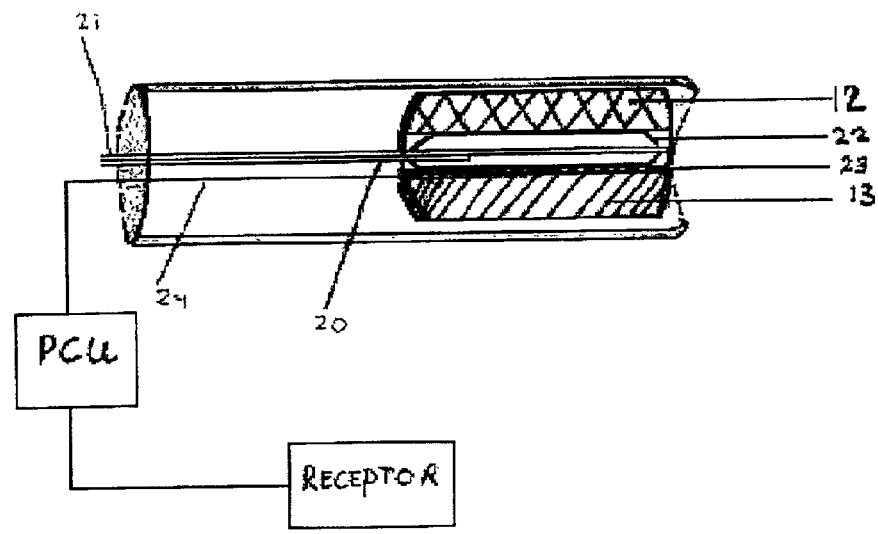
FIG. 3A is a partial cross-sectional view of another preferred embodiment of the drug delivery device, containing an expandable balloon and electrode that is used to expand the polymer matrix of the drug transfer part of the drug delivery device. Here the electrode is positioned in the elongated tubular body, in its non-expanded state when being installed into the epidural space.
Figure 3B:
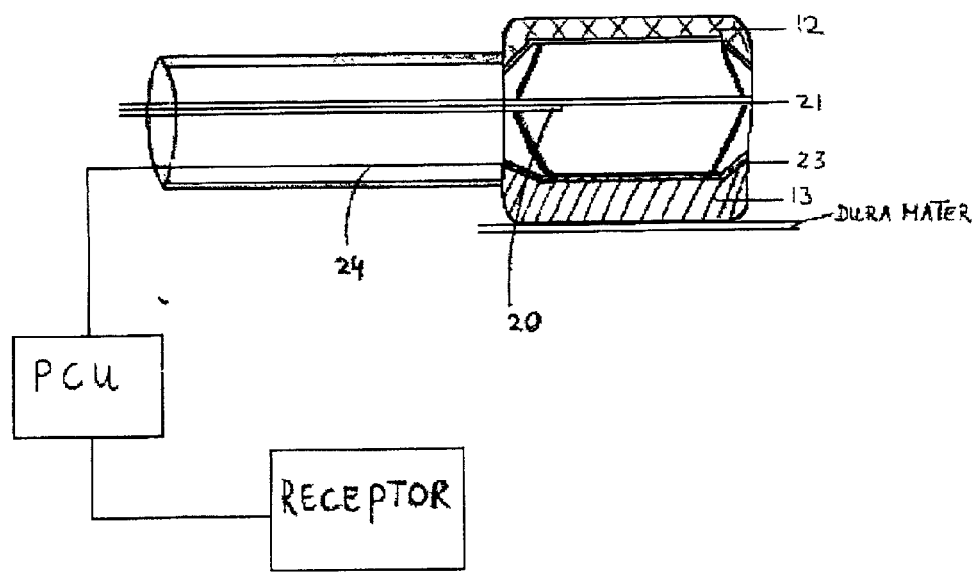
FIG. 3B is a partial cross-sectional view of another preferred embodiment of the drug delivery device, containing an expandable balloon and electrode that is used to expand the polymer matrix of the drug transfer part of the drug delivery device. Shown is its expanded state.

3. The drug reservoir or drug transfer part becomes expanded due to inflation of a preferably cylindrical shaped balloon on which the drug container (e.g. a polymer matrix) is located. An electrode covers the balloon for example in its medial aspects, thereby allowing for enhanced transport out of the drug transfer part and directly into the epidural space. The electrode may be expandable (e.g. a wire mesh), and may take any form obvious to those skilled in the art. In one example, the balloon 22 is inflated by fluid or gas through lumen 20 (FIG. 3A). In its expanded state (FIG. 3B) electrode 23 expands with balloon 22. The part of the electrode that is in touch with the balloon or any other expandable mean is composed of a layer of insulating material. The polymer matrix 13 serves as a drug reservoir or drug transfer part in this example. Electric current is provided to the electrode 23 using wire 24, which runs alongside lumen 20.

The membrane that comprises the wall of the balloon is preferably made of an impermeable material (prevents the flow of water or electrolyte and any component of the drug transfer part or reservoir in any direction).

The drug delivery part of the device is shaped following expansion according to the human epidural space in order to provide the best fit in the epidural space, which is necessary for an intimate contact between the device and the dura mater.

The balloon is attached along either anterior or posterior end to the body of the device using an adhesive or heat weld or other means known to those skilled in the art. The drug reservoir or the drug transfer part is disposed on the outer surface of the balloon that is positioned towards the spinal cord for intimate contact with the dura mater after expansion. In use, the balloon 22 is expanded with a fluid supplied through fluid-supply lumen 20. The fluid used to expand the balloon 22 is water, or a solution, preferably an aqueous-based solution, more preferred an electrolyte solution such as sodium chloride (saline), most preferably a weak electrolyte solution. However, the balloon 22 may be expanded with any possible fluid or gas for use in catheters with expandable means known to those skilled in the art, but preferably suitable to provide for long-term inflation such as required for use according to the present invention.

In an alternative embodiment the device is substantially similar to the device shown in FIG. 2 but with the substitution of an ultrasound transducer for the electrode 9. The iontophoresis electrode is replaced by an ultrasonic piezoelectric transducer (barium titanate, lead zirconate titanate, or the like), which is connected to the PCU. After the drug delivery device is in place, the ultrasonic transducer is activated to transport the biologically active agent into the surrounding spinal structures and the brain. The transducer is used to produce sonic energy, which moves the biologically active agent directly from the drug transfer part 13 to the dura mater, and/or enhance penetration of the biologically active agent through the dura mater and into the adjacent spinal tissues as well as into the CNS. Any type of drug reservoir or drug transfer part containing the drug transfer surface disclosed above can be used instead of the polymer matrix. Here, phonophoresis is used instead of iontophoresis.

In another preferred embodiment, the drug delivery device includes a flexible body and a drug reservoir or a drug-containing transfer material comprising a drug transfer surface (e.g. composed of a polymer matrix). Positioned in the polymer matrix is an electrode, which is connected to a wire, which extends to the proximal end of the tubular member. Instead of the polymer matrix, any material can be used but preferably that with good elastic properties so that it can assume the shape of the epidural space in order to provide an intimate contact between the drug transfer surface and the dura mater. Any design, size or material of the electrode known to those skilled in the art can be used in this embodiment but the important feature is that the device fits comfortably and for a long time period into the epidural space of the subject and provides an intimate contact with the dura mater.

Figure 4:
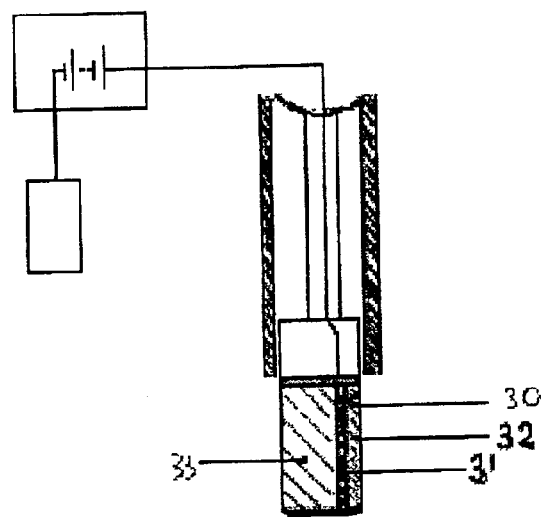
FIG. 4 is a schematic side view of a preferred embodiment of the disclosed delivery apparatus that has no expandable means.

FIG. 4 shows an example of a device that could implement the disclosed method without expandable means. There is shown a proposed catheter-based drug delivery device that is arranged and constructed in such a way that it can be optimally positioned into the human epidural space for iontophoretic and/or phonophoretic transport of a biologically active agent through the dura mater into the adjacent spinal structures and brain. The donor electrode of the drug delivery device is advanced out of the catheter when it has reached the epidural space and when it has assumed the correct orientation. Alternatively, the catheter itself may be removed and leaving the donor electrode implanted. The donor electrode comprises an electrode 30 having an electroconductive part 31 and an electric insulating backing layer 32 that is impermeable and biocompatible. The drug reservoir or transfer part 33 being preferably a polymer matrix that is capable to release the biologically active agent upon application of an electric field. Most preferably, the drug reservoir has such properties that it is only permeable for drug and electrolyte transport during current application and is impermeable for both electrolytes and the biologically active agent when there is no current transport.

In addition, drug reservoirs and/or drug transfer parts, which can be filled with a liquid composition containing the biologically active agent through additional lumens (extending from the proximal end towards the drug reservoir and/or drug transfer part at the distal end of the device) may be used. Thereby allowing the liquid composition in the drug reservoir or drug transfer part of the device to be replaced continuously or at appropriate times. Thus providing an alternative drug delivery system, which can be used for long-term, enhanced drug delivery.

With respect to the polymer composition, the term "polymer matrix" as used herein includes synthetic hydrogel polymers with pores or interstices of different sizes and capacities introduced during manufacture, and a variety of synthetic elastomers and naturally occurring polymeric materials known to those skilled in the art. The biologically active agent can be incorporated in the matrix either during polymer production or added after coating or molding of the polymer into the desired shape. Additionally, many of a number of different polymeric materials and methods of fabrication may be used to form the polymeric matrices used in the present invention. Examples of suitable polymer materials or combinations include, but are not limited to, biocompatible and/or biodegradable polymers such as poly (lactides), polyglycolides, polyanhydrides, polyorthoesters, polyactals, polydihydropyrans, polycyanoacrylates and copolymers of these and polyethylene glycol. These can take the form of copolymer hydrogels or cross-linked polymer networks into which drugs for electrically enhanced local delivery can be incorporated either during polymerisation or, in the case of certain hydrogels, loaded subsequently. Preferable matrices would be tailored according to the molecular characteristics of the agent to restrict its loss by free diffusion outwards, but allow full iontophoretic migration outwards when a potential is applied across the polymer and adjacent tissue.

With respect to the electroconductive members or electrodes, which can be used in the present invention, they are comprised of electrically conductive material such as a metal like aluminium, stainless steel, gold, silver, titanium, and zinc. Examples of other suitable electrically conductive materials include but are not limited to: carbon, graphite, and metal salts like silver chloride. Electrodes may be formed of metal foil, metal screen, metal deposited or painted on a suitable carrier backing by means of calendaring, film evaporation, or by mixing the electrically conductive material in a polymer binder matrix.

Alternatively, electrodes may be formed of a polymer matrix containing conductive filler such as a metal powder, powdered graphite, carbon fibers, or other known electrically conductive filler material. Polymer based electrodes may be manufactured by mixing the conductive filler in a polymer matrix, preferably a mixture of hydrophilic and hydrophobic polymers. The hydrophobic polymers provide structural integrity, while the hydrophilic polymers may enhance ion transport. For example, metal powder, carbon powdered, carbon fibers and mixtures thereof can be mixed in a hydrophobic polymer matrix.

The donor and receptor electrode can be made of any suitable material or combination of materials, that fulfils relevant criteria with respect to compatibility with the biologically active agent in case of a donor electrode and with the biological environment, but also with respect to ease of manufacturing, sterilizability, re-usability, low environmental impact, flexibility, connectibility, disposability and durability. Furthermore, in case of a reservoir-type electrode, the reservoir containing the biologically active agent should be constructed of any material in such way that it is adapted to absorb and hold a sufficient quantity of liquid in order to permit transport of the active agent through its wall by means of iontophoresis. For example sponges, gauzes or pads consisting of cotton or other absorbent fabric, either of natural or synthetic origin, may be used.

More preferably, reservoirs are composed, at least in part, of one or more hydrophilic polymers. Typical preference is for hydrophilic polymers because water is the preferred ion transport medium and hydrophilic polymers have relatively high equilibrium water content. Multilayered solid polymer reservoir matrices are composed, at least in part of hydrophilic polymer. The form, size and shape of the donor electrode and its drug reservoir are determined by the physiological, anatomical environment related to the application site.

In one embodiment of the device, solid or semisolid material(s) is used as the drug reservoir and/or drug transfer part (e.g. gel, polymer matrix or membrane) when located in the expandable part of the device it should be made of a compliant and expandable material (regardless of the mechanism of expansion), ideally minimally compressible. The compressibility of the material is preferably limited to ensure intimate contact between the drug transfer surface and the dura mater to enhance drug transfer and decrease side effects. In an alternative embodiment, the material could be compressible, provided the expandable part is designed in such a way that there is intimate contact after expansion despite of the compressibility of the material.

In the embodiments, which do not expand, radial, the material does not need to be expandable. However, in such embodiments the plasticity properties of the material are important and the material may be compressible in order to better mold to the anatomy of the epidural space and preferably to provide a better contact interface with the dura mater.

In a preferred embodiment, the drug transfer surface is located in the expandable part, which allows radial or unidirectional (ventral i.e. towards the dura mater) expansion of the device or part of the device containing the drug transfer surface after the device has been advanced to an appropriate depth so that following expansion the drug transfer surface forms an intimate contact interface with the dura mater.

The power supply used in conjunction with the present invention can be any small-size and lightweight cell. For example, the cells include manganese cells, alkali cells, lithium cells, unicad cells, silver oxide cells, mercury cells, air cells, alkali-manganese cells and plastic cells. Plastic cells are formed into button shape or sheet.

The drug reservoir or drug transfer part or other contact surface that is directly involved in the drug transfer of each of the described possible embodiments may optionally contain penetration enhancing substance(s) and/or enzyme inhibitors, either as part of the pharmaceutical composition or as part of the polymer matrix or drug reservoir membrane or drug transfer part of the device, to further enhance the drug transport through the epidural space or dura mater into the adjacent spinal tissue and into the CNS.

The drug delivery device is positioned within the tubular member during its installation to the target area in the epidural space. The drug reservoir or drug transfer part of the disclosed drug delivery device can be placed by pushing the drug delivery device out of the tubular body until it reaches a predetermined point beyond the drug delivery device may not be further advanced outwards. The elongated tubular body thus provides a means of protection to the drug delivery device and especially to the drug reservoir or drug transfer part, during installation and removal of the device. It will be understood, that instead of pushing the drug delivery device out of the tubular member, the latter can also be pulled back to expose the drug reservoir or drug transfer part in the epidural space, which will in possible alternative embodiments of the present invention lead to a comparable result.

The tubular body being constructed from electrically insulating, biocompatible material and further being flexible to facilitate the insertion through the narrow epidural space.

Alternative to the described tubular body, it may be equipped with means to allow for endoscopic controlled installation of the drug delivery device. For example, it may contain besides the drug delivery device an optic fiber or any other possible imaging means known by those skilled in the art.

In another preferred embodiment of the present invention, the drug delivery device or a part of it i.e. the drug reservoir or drug transfer part is placed at its target site in the epidural space, whereas the tubular body is removed. The drug delivery device or a part of it may thus be implanted in the epidural space but be connected to the PCU. At appropriate times, depending on the treatment the device or part of it is replaced. The device or part of it may be placed at its target site possibly under endoscopic control by means of sutures, adhesives or other semi-permanent or permanent connections.

It will now be apparent to those skilled in the art that other embodiments, improvements, details, and uses can be made consistent with the letter and spirit of the foregoing disclosure and within the scope of this patent, which is limited only by the following claims, construed in accordance with the patent law, including the doctrine of equivalents.

What is claimed is:

1. A method for enhanced and controlled delivery of a biologically active agent into the spinal structures and/or the brain of a mammal, particularly a human being that circumvents the blood brain barrier, which includes the steps of:

providing an agent drug delivery device via catheter to the epidural space of the mammal and positioning said device within the epidural space, advancing a donor iontophoresis electrode into the epidural space of the mammal, applying a second electrode or receptor iontophoresis electrode that is constructed and arranged to be positioned at a determined internal or external position of the mammal's body but in complementary energy gradient positioning to the first electrode, providing a potential gradient so that delivery of the biologically active agent is accomplished in a direction from said first electrode means directly into the spinal structures and/or the brain thereby essentially bypassing the blood brain barrier of the mammal; and thereby, delivering said biologically active agent directly to the spinal structures and/or to the brain of said mammal.

2. A method for enhanced and controlled delivery of a biologically active agent into the spinal structures and/or the brain of a mammal, particularly a human being that circumvents the blood brain barrier, which includes the steps of:

providing an agent drug delivery device via catheter to the epidural space of the mammal and positioning said device within the epidural space, advancing a phonophoresis device in the epidural space of the mammal, providing an energy gradient so that delivery of the biologically active agent is accomplished in a direction from said phonophoresis device directly into the spinal structures and/or the brain thereby essentially bypassing the blood brain barrier of the mammal, and thereby, delivering said biologically active agent to the spinal structures and/or to the brain of said mammal.

3. A method as claimed in claim 1 wherein a biosensor is used for feedback regulated delivery of the biologically active agent to the spinal structures and/or brain of the mammal.

4. A method as claimed in claim 3 wherein the biosensor is used for feedback regulated delivery of the biologically active agent in the treatment of chronic pain.

5. A method, using an implantable device, for enhanced and controlled delivery of a biologically active agent into the spinal structures and/or the brain of a mammal, particularly a human being, and that circumvents the systemic circulation, which comprises the steps of:

(i) directing at least one end of a catheter containing a delivery device to the epidural space of a mammal and positioning said catheter and delivery device within the epidural space to provide an effective arrangement for delivering a biologically active agent which is contained in said device into the mammal;

(ii) advancing a first electrode from said delivery device that is constructed and arranged to be positioned in the epidural space of a mammal into the epidural space of a mammal and act as a donor electrode;

(iii) applying a second electrode that is constructed and arranged to be positioned at a determined internal or external position of the mammal's body and act as a receptor electrode;

(iv) electrically connecting said first and second electrodes to a power control unit that includes an integrated (pre)-programmable power source, the power source being operated by a microprocessor, said power source providing a potential gradient so that delivery of a biologically active agent is accomplished in a direction from said first electrode directly into the spinal structures and/or the brain thereby essentially bypassing the systemic circulation of a mammal; and (v) delivering said biologically active agent to the spinal structures and/or to the brain of said mammal using an active transport means.

6. A method according to claim 5 wherein the active transport means is iontophoresis and/or phonophoresis.

7. A method according to claim 5 wherein said power source provides an electro-potential gradient or ultrasound.

8. A method as claimed in claim 5 wherein a biosensor is connected to the power control unit for feedback regulated delivery of a biologically active agent to the spinal structures and/or the brain of a mammal.

9. A method as claimed in claim 8 wherein the biosensor is adapted to register biopotentials for feedback regulated delivery of a biologically active agent in the treatment of chronic pain, hyperkinesis or any other pathological symptoms or diseases.

10. A method as claimed in claim 5 wherein the donor electrode includes a drug reservoir or drug transfer part for storage of the biologically active agent, an impermeable part that is not involved in drug transfer, and an electroconductive member.

11. A method as claimed in claim 5 wherein the receptor electrode is an iontophoresis electrode which includes an electrolyte-containing compartment for storage of electrolyte, an electroconductive member and a membrane through which electrolyte transport occurs.

12. A method according to claim 5 that includes a means for in situ refilling of said device.

13. A method as claimed in claim 5 wherein the donor electrode includes a means for expansion thereby allowing the drug reservoir or transfer part to make an intimate contact with the dura mater.

14. A method as claimed in claim 5 wherein an expansion means is operably connected to the drug delivery device, the expansion means being configured to expand the donor electrode in a direction substantially radial thereby promoting an improved contact interface between the drug reservoir or transfer part and the dura mater.

15. A method as claimed in claim 12 wherein an expansion means is provided by reversible swelling properties of the drug reservoir or transfer part that is induced by chemical or physical changes such as for example, electric current, pH, temperature or any combinations thereof.

16. A method as claimed in claim 5 wherein the drug delivery part of the device is shaped following expansion according to the human epidural space.

17. A method according to claim 5 wherein said first electrode is a reservoir-type iontophoresis electrode holding a supply of the selected biologically active agent in a formulation suitable for iontophoretic or phonophoretic delivery and/or wherein said second electrode is a reservoir-type iontophoresis electrode holding a supply of electrolyte.

18. A method according to claim 5, wherein said first and second electrodes comprise an electroconductive part having electroconductive material selected from the following group: stainless steel, gold, silver, titanium, copper, zinc, graphite and metal salts (e.g. silver chloride).

19. A method according to claim 5 wherein said reservoir of said first and/or second electrode means is formed of a polymer matrix containing an electroconductive filler material selected from the group consisting of a metal powder, powdered graphite and carbon fibers.

20. A method according to claim 17 wherein said reservoir is constructed of material that is adapted to absorb, hold and release the biologically active agent and/or electrolyte.

21. A method according to claim 17 wherein said reservoir is made of a hydrogel that holds the biologically active agent and/or electrolyte.

22. A method according to claim 5 wherein the catheter-based device includes a mean for endoscopic controlled installation such as an optic fiber.

23. A method according to claim 5 wherein the catheter-based device can be removed entirely from the epidural space following positioning of the donor electrode.

* * * * *